United States Patent [19]
Werneth et al.

[11] Patent Number: 6,056,906
[45] Date of Patent: *May 2, 2000

[54] METHOD OF MAKING AN INTERVASCULAR CATHETER SYSTEM FOR IMPLANTING A RADIALLY EXPANDABLE STENT WITHIN A BODY VESSEL

[75] Inventors: Randell L. Werneth; John J. Bridgeman; Gary E. Currie, all of San Diego, Calif.

[73] Assignee: Medtronic, Inc., Minneapolis, Minn.

[*] Notice: This patent is subject to a terminal disclaimer.

[21] Appl. No.: 08/978,711

[22] Filed: Nov. 26, 1997

Related U.S. Application Data

[62] Division of application No. 08/723,084, Sep. 25, 1996.
[51] Int. Cl.$^7$ .............................. B29C 41/22; B29C 47/06
[52] U.S. Cl. .................... 264/135; 264/171.26; 264/249; 425/517
[58] Field of Search ...................................... 264/134, 249, 264/255, 293, 171.26, 135; 475/508, 517

[56] References Cited

U.S. PATENT DOCUMENTS

| | | |
|---|---|---|
| 1,777,571 | 10/1930 | McCullough . |
| 3,515,777 | 6/1970 | Holthaus . |
| 3,541,682 | 11/1970 | Hildebrandt . |
| 4,886,062 | 12/1989 | Wiktor . |
| 4,950,227 | 8/1990 | Savin et al. ................................. 604/8 |
| 5,026,377 | 6/1991 | Burton et al. ............................. 606/108 |
| 5,042,143 | 8/1991 | Holleman et al. ......................... 29/825 |
| 5,100,429 | 3/1992 | Sinofsky et al. .......................... 606/195 |
| 5,108,416 | 4/1992 | Ryan et al. ............................... 606/194 |
| 5,163,958 | 11/1992 | Pinchuk ...................................... 623/11 |
| 5,409,495 | 4/1995 | Osborn ..................................... 606/108 |
| 5,484,411 | 1/1996 | Inderbitzen et al. ........................ 604/96 |
| 5,484,449 | 1/1996 | Amundson et al. ...................... 606/108 |
| 5,514,154 | 5/1996 | Lau et al. ................................. 606/195 |
| 5,545,132 | 8/1996 | Fagan et al. ................................ 604/96 |
| 5,569,295 | 10/1996 | Lam ........................................ 606/198 |
| 5,613,979 | 3/1997 | Trotta et al. ............................. 606/194 |
| 5,653,691 | 8/1997 | Rupp et al. ................................. 604/96 |
| 5,807,327 | 9/1998 | Green et al. ............................... 604/96 |

FOREIGN PATENT DOCUMENTS

| | | | |
|---|---|---|---|
| 0 553 960 | 8/1993 | European Pat. Off. .......... A61F 2/06 |
| 0 705 576 | 9/1995 | European Pat. Off. .......... A61F 2/06 |
| 0 689 807 | 1/1996 | European Pat. Off. .......... A61F 2/06 |
| WO 95/33422 | 12/1995 | WIPO ............................... A61F 2/06 |
| WO 96/12450 | 4/1996 | WIPO ............................... A61F 2/06 |

OTHER PUBLICATIONS http://matweb.com/; provides properties for PET, Polyethylene terephthalate, 1997.
http://matweb.com/; provides properties for polyurethane, cast, liquid, 1997.
Roff and Scott, Handbook of Common Polymers; p. 454 (melt temperature of polyurethane), 1971.

*Primary Examiner*—Jan H. Silbaugh
*Assistant Examiner*—Edmund H. Lee
*Attorney, Agent, or Firm*—Dianne Plunkett Latham; Harold R. Patton

[57] ABSTRACT

An intravascular catheter system and method of manufacture for implanting a radially expandable stent within a body vessel. The catheter system includes a shaft defining an inflation lumen in fluid communication with a balloon on the distal end of the shaft. A stent is mounted coaxially upon a balloon. The balloon has ridges impressed in the outline of the stent for at least a portion of the stent. The ridges are sized to receive the stent so as to cause the balloon to expand evenly and the stent to deploy uniformly. In an alternative embodiment the balloon may additionally have a polymeric surface layer exhibiting a higher coefficient of friction than the underlying material against the stent material. The surface layer may be provided as a high friction polymeric coating on a formed balloon or as a coaxial extrusion of a high friction polymeric material over the underlying balloon tubing material. In a further embodiment the balloon may have the polymeric surface layer exhibiting a higher coefficient of friction than the underlying material against the stent material but without the ridges.

8 Claims, 7 Drawing Sheets

METHOD OF MAKING AN INTERVASCULAR CATHETER SYSTEM FOR IMPLANTING A RADIALLY EXPANDABLE STENT WITHIN A BODY VESSEL

This is a divisional of copending application Ser. No. 08/723,084 filed on Sep. 25, 1996.

FIELD OF THE INVENTION

The present invention relates to an intravascular stent deployment system and method of manufacture and more particularly to a catheter balloon for stent delivery with the stent impression being heatset into the balloon thereby forming ridges to match the stent and/or with a high friction balloon surface. The ridges and/or high friction surface hold the stent in place longitudinally permitting more uniform expansion of the stent and reducing the likelihood of the stent slipping along the balloon, inadvertently dislodging or snagging.

BACKGROUND OF THE INVENTION

Percutaneous transluminal coronary angioplasty (PTCA) is used to reduce arterial build-up of cholesterol fats or atherosclerotic plaque. Typically a first guidewire of about 0.038 inches in diameter is steered through the vascular system to the site of therapy. A guiding catheter, for example, can then be advanced over the first guidewire. The first guidewire is then removed. A balloon catheter on a smaller 0.014 inch diameter guidewire is advanced within the guiding catheter to a point just proximal to the stenosis. The second guidewire is advanced into the stenosis, followed by the balloon at the distal end of the catheter. The balloon is then inflated causing the site of the stenosis to compress into the arterial wall. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from the small coronary vessels to the 28 mm aortic vessel. The invention applies to acute and chronic closure or reclosure of body lumens.

A typical stent is a cylindrically shaped wire formed device intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls.

The biocompatible metal stent props open blocked coronary arteries, keeping them from reclosing after balloon angioplasty. A balloon of appropriate size and pressure is first used to open the lesion. The process is repeated with a stent crimped on a balloon. The stent is deployed when the balloon is inflated. The stent remains as a permanent scaffold after the balloon is withdrawn.

U.S. Pat. No. 4,886,062 to Wiktor for "Intravascular Radially Expandable Stent and Method of Implant" discloses a two-dimensional zig-zag form, typically a sinusoidal form.

U.S. Pat. No. 5,409,495 to Osborn for "Apparatus for Uniformly Implanting a Stent" discloses elastic restraining bands which exert a force at the proximal and distal ends of the balloon equal and opposite to that generated by the combined resistance of the sleeve and the stent tending to deform the balloon. In this way, the uneven expansion (end effects) are limited when the balloon is expanded which, in turn, inhibits a "dog boning" deformation at the proximal and distal regions of the balloon. FIGS. 3–6 show a balloon of complex manufacture.

European Patent No. 553,960 Al to Lau for "Protective membrane for Stent-carrying Balloon Catheter" discloses a stent mounted on a tubular sheath having an outer surface composed of a high coefficient of friction material designed to secure the stent until balloon inflation.

Copending U.S. Ser. No. 08/637,959 to Rupp et al. discloses a balloon catheter for stent delivery with the catheter inner lumen tube having a greater outer diameter for a central portion of the area covered by the stent thereby permitting more uniform expansion of the stent.

As stent metal mass increases in stents having elements that can expand independently in the longitudinal direction, there is a tendency towards longitudinal compression at the center of the stent when expanded. The increased metal mass creates more radial hoop strength which in turn increases the amount of force required to expand the stent. The center of the stent has more radial hoop strength than the ends of the stent. As a result, the balloon expands first at the distal and proximal ends before expanding at the center. This creates a dumbbell shaped balloon. With the stent ends expanding first, the stent slides down the expanded balloon ends toward the center of the balloon which is as yet unexpanded because of the stent's greater radial hoop strength in the center. When the balloon ends have expanded completely, the deployed stent may be compressed to length that is significantly shorter than desired. Because the stent is compressed toward the center of the balloon, complete balloon expansion may not be possible. Due to the nature of the PTCA procedure, as well as handling prior to the procedure, there exists a potential for inadvertent dislodgment of the stent caused by slippage of the stent along the deflated balloon.

Bare stenting without a stent sheath presents the additional problem of the stent snagging upon luminal calcification. What is needed is a method of stent deployment which results in uniform stent expansion and reduces the likelihood of the stent slipping along the balloon, inadvertently dislodging or snagging.

SUMMARY OF THE INVENTION

It is an object of the invention to provide a catheter system for implanting a radially expandable stent which reduces longitudinal stent slippage during stent expansion, reduces snagging during insertion and permits uniform radial stent expansion. The present invention is accomplished by providing an intravascular catheter system and method of manufacture for implanting a radially expandable stent within a body vessel. The catheter system comprises a shaft defining an inflation lumen in fluid communication with a balloon on the distal end of the shaft. A stent is coaxially mounted on the balloon. The balloon has ridges impressed in the outline of the stent for at least a portion of the stent. The ridges are sized to receive the stent so as to reduce stent slippage and cause the balloon to expand evenly and the stent to deploy uniformly. In an alternative embodiment the balloon may additionally have a polymeric surface layer over an underlying material. The surface layer having a higher coefficient of friction than the underlying layer. The surface layer may be provided as a high friction polymeric coating on a formed balloon or as a coaxial extrusion of a high friction polymeric material over the underlying balloon tubing material. In a further embodiment the balloon may have the polymeric surface layer but without the ridges.

DETAILED DESCRIPTION OF THE PREFERRED EMBODIMENTS

Figure 1:
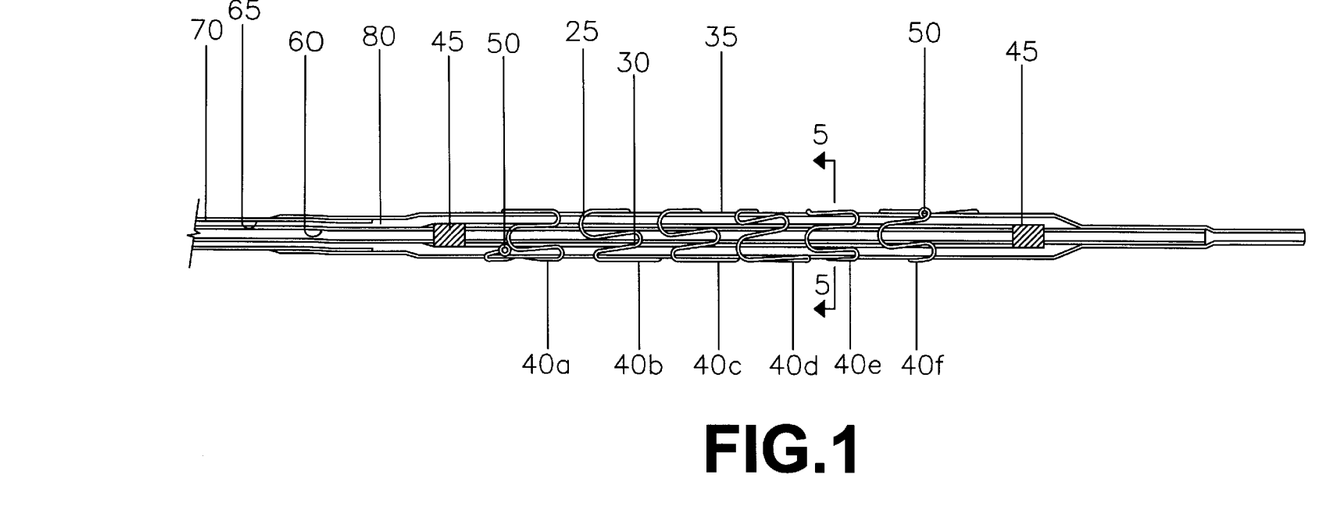
FIG. 1 is a side elevation overall view of a stent fitted over a longitudinal cross-section of a deflated balloon.
Figures 2, 4:
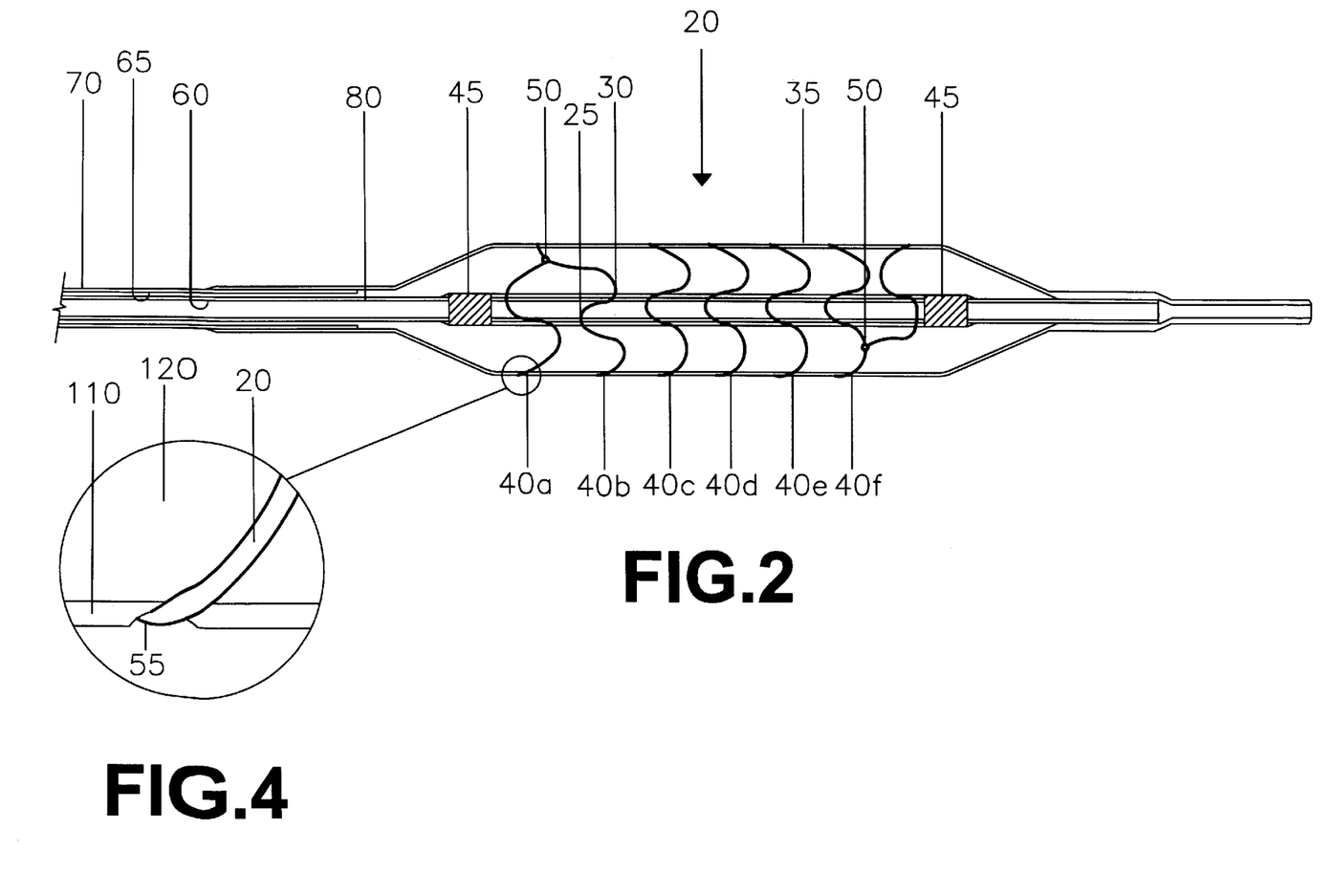
FIG. 2 is a side elevation overall view of a stent fitted over an inflated balloon.
FIG. 4 is an enlargement of a portion of FIG. 2.

Refer to FIG. 1 showing a side elevation overall view of a Medtronic Wiktor stent 20 fitted over a longitudinal cross section of a deflated balloon 35. The Wiktor stent 20 is formed with a wire which is formed into zig-zags such as a sinusoidal wave form helix pattern the length of the stent by a means such as passing the wire through gears such as those disclosed in U.S. Pat. No. 2,153,936 issued to Owens et al. The zig-zags are formed by alternate peaks 25 and valleys 30. The zig-zags are canted toward the proximal and distal ends of the stent 20. The zig-zags form a plurality of spaced-apart elements 40a–f each extending 360 degrees around the hollow cylinder. Each of the elements 40a–f has a plurality of extendible portions such as the zig-zags which permit the wire elements 40a–f to be expanded from an unexpanded diameter as seen in FIG. 1 to a second, expanded diameter as seen in FIG. 2.

A wire having formed zig-zags is wound around a forming mandrel to create the cylindrical stent shape. After the stent has been reduced to the objective outer diameter by compressing it on successively smaller mandrels, the proximal and distal ends of the wire segment are attached. The means of attachment may include looping 50 the end segments together, twisting, biocompatible adhesive, brazing, welding or stamping.

For coronary applications, the stent 20 wire can have a diameter of about 0.001 inches to about 0.015 inches. The balloon expandable stent can be made of an inert, biocompatible material with high corrosion resistance that can be plastically deformed at low-moderate stress levels such as tantalum, the preferred embodiment. Other acceptable materials include stainless steel, titanium ASTM F63–83 Grade 1, niobium or high carat gold K19–22. A self-expanding device can be made by the use of superelastic nickel titanium (NiTi) such as Nitinol manufactured by Raychem or Forukawa.

The preferred form of the sinusoidal wave of the stent wire for coronary applications is a length of about 0.150 inches to about 0.090 inches and a wave amplitude of between about 0.050 inches and about 0.080 inches. Any wave length and amplitude combination that would provide adequate vessel hoop strength and vessel coverage is appropriate. The stent of this invention and balloon can be transported via a standard #7 or 8 French guiding catheter. Once on location, the stent can be expanded radially by the expansion of the balloon 35; a ratio of 2.75:1 can be achieved with a wire diameter of approximately 0.005 inches and an initial stent diameter of approximately 0.060 inches.

As seen in FIG. 1, the stent 20 is centrally located and positioned with respect to the length of balloon 35. The stent 20 turns are evenly spaced so that when the stent 20 is expanded the stent 20 will provide even support inside the vessel and resist external loading. The stent 20 must expand evenly and permit the balloon 35 to expand evenly.

The Wiktor stent is formed of a hollow cylindrical wire winding having a plurality of spaced-apart circumferential elements 40a–f. Each element 40a–f extends 360 degrees around the hollow cylinder such that the elements 40a–f can move longitudinally as the stent 20 is expanded. Each of the elements 40a–f has a plurality of extendible portions 25, 30 which permit the wire elements 40a–f to be expanded. Each peak 25 and valley 30 pair comprises a wave. To achieve greater coverage, metal mass can be increased in a sinusoidal wave form stent 20 by having more waves per revolution, as for example, increasing from four waves to six waves. Stents such as that shown in FIG. 1 having elements 40a–f can expand independently in the longitudinal direction and can present special problems not presented by stents formed of a solid cylinder.

As stent metal mass increases in stents with extendible portions, there is a tendency towards longitudinal compression at the center of the stent when expanded. The increased metal mass creates more radial hoop strength which in turn increases the amount of force required to expand the stent 20. The center of the stent has more radial hoop strength than the ends of the stent 20. The balloon expands first at the distal and proximal ends before expanding the center which is covered by the stent. This creates a dumbbell shaped balloon. With the stent ends expanding first, the stent slides down the expanded balloon ends toward the center of the balloon which is as yet unexpanded because of the stent's increased radial hoop strength in the center. As the proximal and distal ends of the balloon expand to approximately two-thirds of normal expansion diameter, the mid-section of the balloon begins to expand. When the balloon ends have expanded completely, the stent may have been compressed to approximately one-half of its original crimped length. This type of balloon inflation seems to act as a moving "snow plow" forcing the stent to slide and contract longitudinally along the balloon. The resulting deployed stent may be tightly bunched, misshapen and significantly shorter than a properly deployed stent. Because the stent is compressed toward the center of the balloon, complete balloon expansion may not be possible.

To prevent the dumbbell effect as well as reducing the chance of stent dislodgment or snagging, the stent may be embedded into the wrapped balloon and/or the balloon surface may be modified in order to increase the coefficient of friction to the point that the forces involved in the longitudinal slippage or inadvertent dislodgment of the stent would not be able to overcome the friction force. The force required to dislodge the stent 20 is therefore increased. If a stent dislodges from the catheter, it could be carried away into the blood stream with serious consequences to the patient. Bare stenting without a stent sheath presents the additional problem of the stent snagging upon luminal calcification. Recessing the stent reduces stent profile and the likelihood of snagging.

Figure 3:
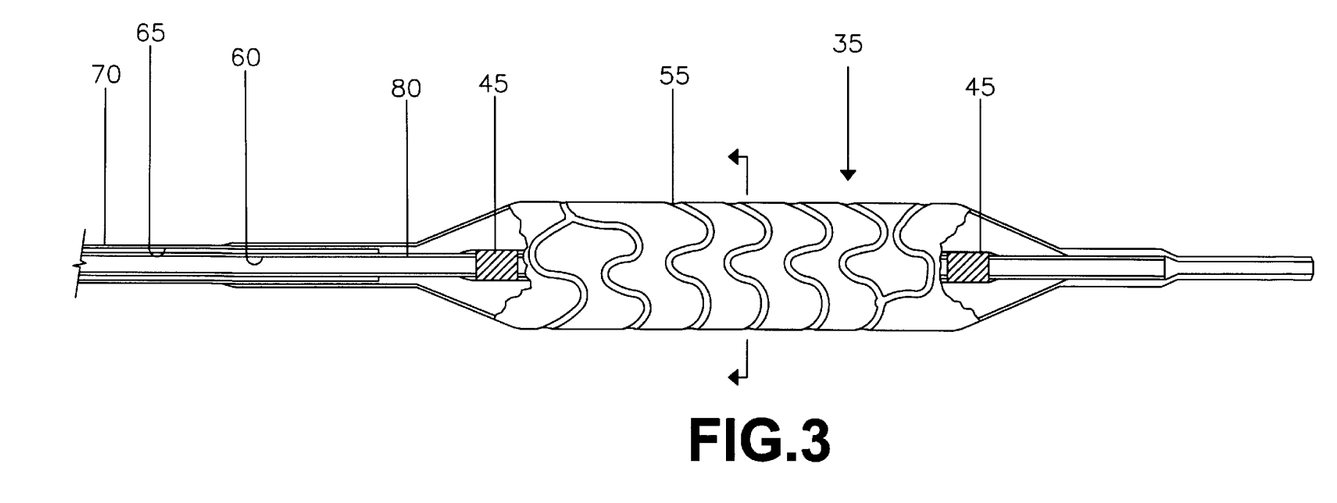
FIG. 3 is a side elevation partially cut-away view of an inflated balloon after the stent has been heat set into the balloon and removed.

The stent can be embedded either directly into the balloon as seen in FIG. 3 or into an external polymeric surface layer 110 as seen in FIG. 4. This can be done by using a heat chamber 75, a crimper 85/100 or a probe 95. When the balloon 35 is expanded to deploy the stent 20, the ridges 55 created by the heated stent 20 hold the stent 20 in place longitudinally and allow the stent to expand without significantly shortening. For any of these methods the balloon 35 must first be wrapped then optionally heatset in any conventional manner.

Figure 5:
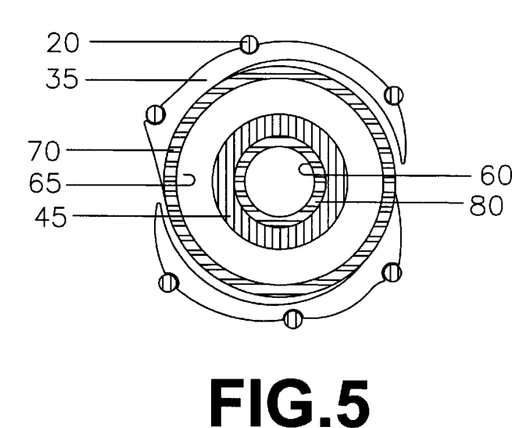
FIG. 5 is a cross-section of FIG. 1 along the lines 5—5.

To wrap the balloon 35 as shown in FIG. 5, the following procedure can be used. For coronary applications, begin with a 0.0160 inch diameter heat set mandrel. A heat set mandrel is TEFLON® coated as opposed to a stainless steal mandrel, for example. TEFLON® does not stick and makes the mandrel easier to remove. TEFLON®, a form of polytetrafluoroethylene (PTFE) is available from E.I. Du Pont de Nemours & Company, Wilmington, Del. Next attach the catheter inflation port to the vacuum manifold. Insert the 10–30 cm mandrel into the distal end of the catheter leaving approximately 10–20 mm of the mandrel extending from the distal tip of the balloon. Deflate the balloon using a vacuum. Fold the balloon so that it wraps evenly around the guidewire tube in an "S" folding pattern as seen in FIG. 5. With vacuum applied and the balloon 35 folded, slide a heat set sleeve over the balloon to hold the balloon in place. Insert the distal end of the catheter into a heat chamber. A heat chamber 75 such as that shown in FIG. 7 can be made in any conventional manner as for example, by utilizing an insulated chamber with a time and temperature controller. Apply heat of 75 degrees F. (1 degree C.) for 10 minutes under a vacuum of a minimum of 24 inches Hg. Allow the balloon to cool for 5 minutes then remove it from the heat chamber and disconnect from the vacuum source. The stent 20 can then be crimped upon the wrapped and heatset balloon 35 either manually or with an appropriate tool.

Figure 6:
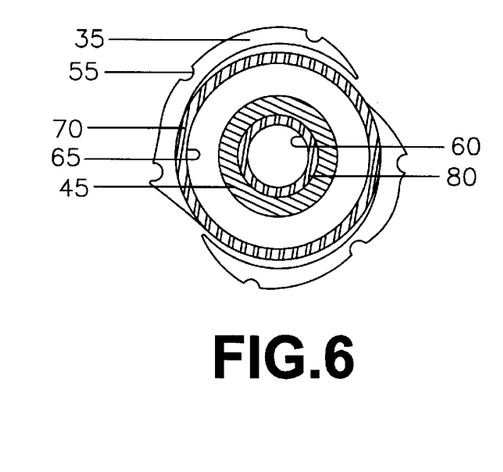
FIG. 6 is a cross-section of FIG. 3 along the lines 6—6.
Figure 7:
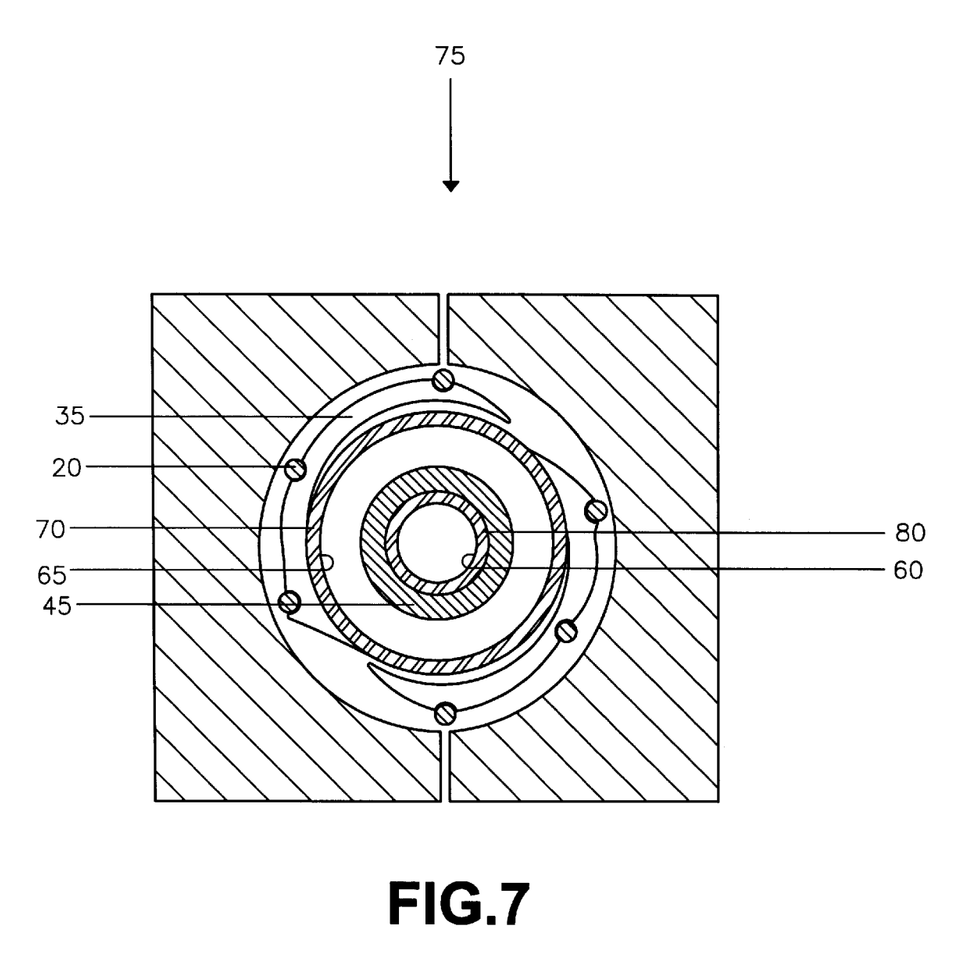
FIG. 7 is a cross-section of a heat chamber with a stent fitted over a deflated balloon therein.

Once the balloon 35 is wrapped, optionally heatset, and has had the stent 20 crimped about it, the balloon 35 and stent 20 may be placed into a heater block type of heat chamber 75 such as that shown in FIG. 7. The heat chamber 75 can be one or two pieces and may be made of aluminum. The chamber 75 inside diameter is less than the outside diameter of the wrapped balloon 35 with stent 20 crimped thereon. The chamber 75 is in contact with the stent 20 thereby heating the stent wire 20 which becomes slightly embedded into the balloon 35. As seen in FIGS. 3 and 6, this creates ridges 55 in the balloon 35 which match the stent 20.

Figure 8:
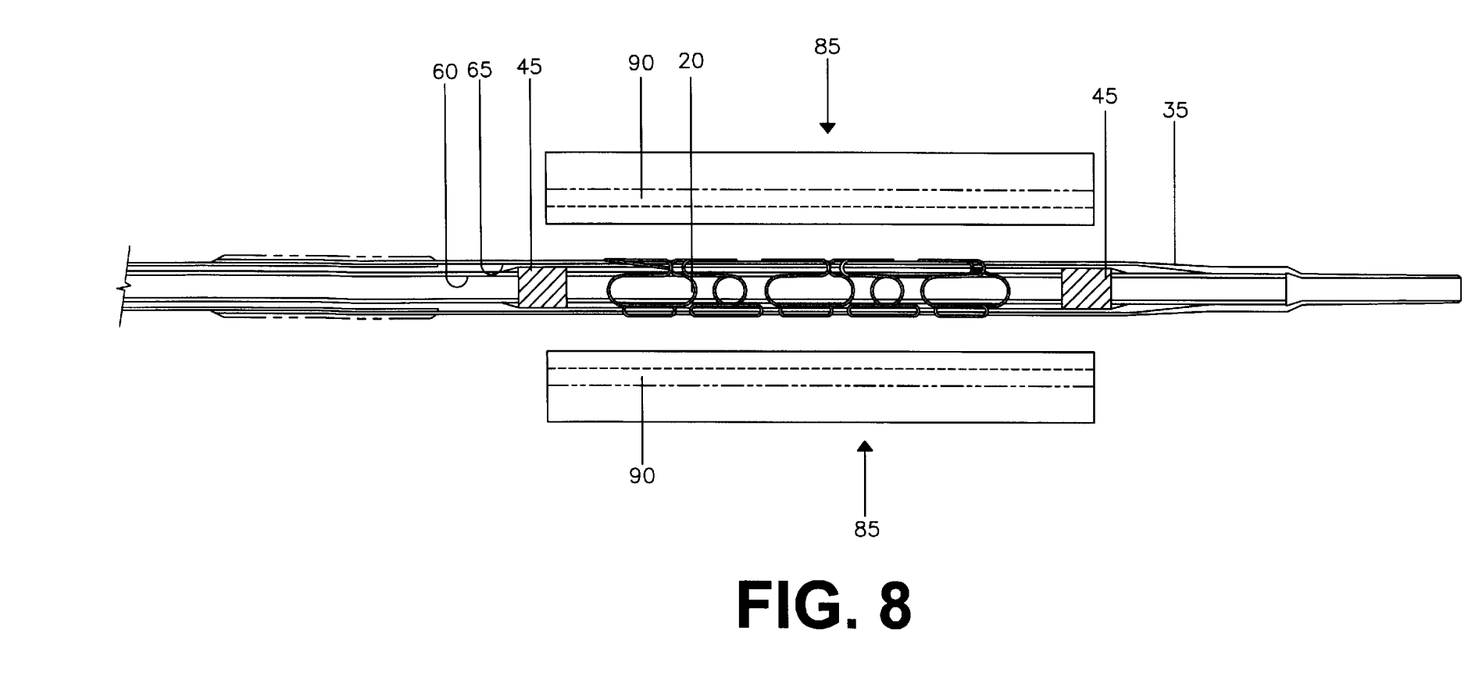
FIG. 8 is a side elevation overall view of a stent fitted over a longitudinal cross-section of a deflated balloon and a crimper with an embedded wire.
Figure 9:
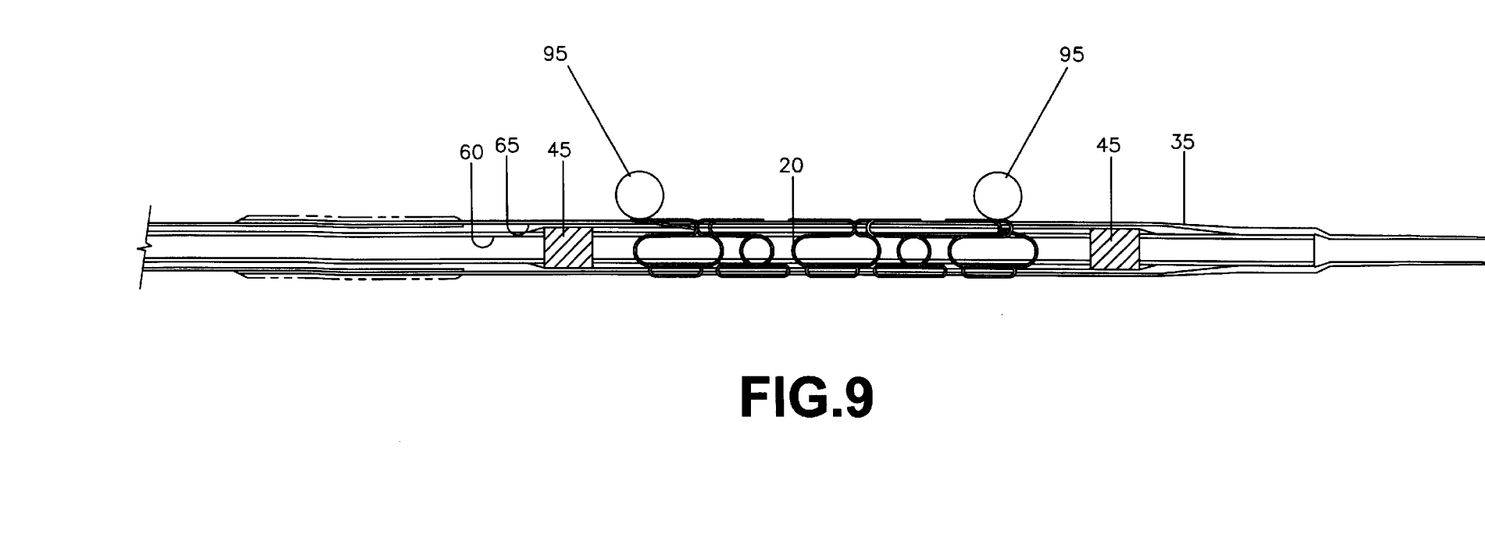
FIG. 9 is a side elevation overall view of a stent fitted over a longitudinal cross-section of a deflated balloon with a probe.
Figure 10:
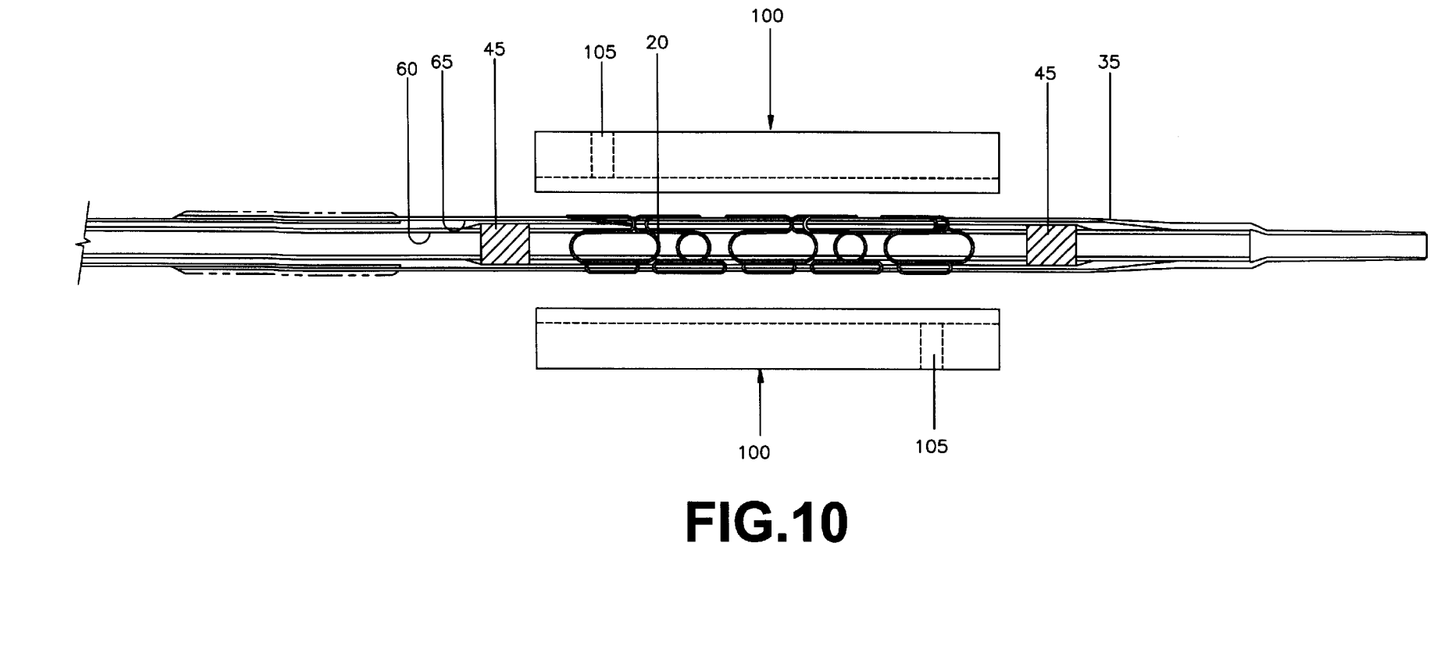
FIG. 10 is a side elevation overall view of a stent fitted over a longitudinal cross-section of a deflated balloon and a crimper with an embedded probe.

An alternative method for embedding the stent 20 into the balloon 35 can be used during the final crimping sequence. This procedure utilizes a crimping device as seen in FIGS. 8 or 10 or a probe as seen in FIG. 9. Any electrically conductive stent can be utilized, be it metal or polymer. For example, tantalum, nitinol or any type of stainless steel is preferred. To embed the electrically conductive stent, a controlled positive and negative electrical current/charge is applied, in any number of locations and orientations to the stent so that the resistance of the stent causes the stent to heat, thus embedding the stent in the delivery system. This can occur before, during or after the final crimping of the stent. A constant or variable amount of current suitable for the stent and/or balloon materials selected may be used in conjunction with any amount of radial compression necessary to cause any degree of embedment desired.

The crimping device can either utilize embedded wires 90 in the crimping device 85 of FIG. 8 or an embedded probe 105 in the crimping device 100 of FIG. 10. In FIGS. 8–10 the crimping device 85 and 100 or probe 95 comes into direct contact with the stent during the final crimping sequence. The stent is placed upon a wrapped balloon. The balloon need not be heat set. In FIGS. 8–10, a controlled amount of electricity is applied to the stent which will heat the stent and create a greater amount of stent embedding by literally melting the stent into the balloon material. The advantage of utilizing a crimper 85 and 100 or probe 95 to heat the stent as opposed to a heat chamber 75 is that the balloon is not heated. Localized heating of the areas in which the stent comes into contact with the balloon is preferable to heating the entire balloon. Heating the entire balloon may cause shrinking.

A suitable temperature for creating the appropriate depth stent 20 shaped ridges in the balloon 35 is that which is sufficient to reach the melt indicator for the chosen material. If the stent 20 is melted directly into the balloon polyethylene layer, use at least 190 degrees F., the melt indicator for polyethylene. Use a typical polyethylene material in catheter balloons such as Rexene® Resins 1017 or 1011 (available from Rexene of Odessa, Tex.) with a melt index of 2.0. The 190 degree F. temperature should be maintained for about 15 to 30 seconds under pressure applied by clamp weight. Within these ranges shortening is minimal and within 1 mm. Those skilled in the art would recognize that time and temperature vary inversely such that a higher temperature could be applied for a shorter duration. For example, radio frequency (RF) heat could be applied for a very short duration. If the temperature is too high or the time too long, the balloon will not expand to its proper diameter as the ridges 55 will become too deep. This was the case with a temperature of 210 degrees F. (99 degrees C.) at one-and-one-half minutes to two minutes. Deep ridges also risk perforation and balloon bursting under lower pressures.

The depth of the ridges 55 is a function of the balloon surface and thickness as well as stent wire diameter. The diameter of a typical stent wire is about 0.005 inches while the wall thickness of a typical balloon is 0.002 inches. The depth of the ridges 55 should be more than 5% of the stent 20 wire diameter to reduce slippage and less than 50% of the balloon wall thickness to minimize balloon perforations. The ridge 55 depth should preferably range from about 0.00025 inches to 0.001 inches.

The balloon 35 may have a polymeric surface layer 110 formed by coating or formed by coaxial extrusion. The stent 20 may be melted into the polymeric surface layer 110 or melted into the underlying layer 120 as well. If the stent 20 is melted into the polymeric surface layer 110 but not melted into the underlying polyethylene layer 120, conditions appropriate for deforming the polymeric surface layer 110 while not deforming the underlying polyethylene layer 120 are used.

In addition to, or instead of, embedding the stent into the balloon, a high friction balloon surface 110 can be provided over the underlying layer 120 to reduce the likelihood of stent slippage. The underlying layer 120 has a first coefficient of friction and the surface layer 110 a second coefficient of friction. The second coefficient of friction is greater than the first coefficient of friction. Such a high friction surface layer 110 can be provided by either coating the balloon with a high friction polymer carried in an appropriate solvent or by coaxially extruding the surface layer 110. The coefficient of friction of the surface layer 110 against the stent should be high enough to prevent the stent from sliding along the balloon prior to and during the PTCA procedure, but not so high as to inhibit proper release and deployment of the stent. If a stent is embedded into a balloon with a high friction polymeric surface layer 110, the surface would be provided prior to embedding the stent allowing for adequate adhesion of a consistently thin high friction film to the balloon.

One method of providing a high friction surface layer 110 is to dip the PTCA balloon into the solvated polymeric coating material, then allow the solvent to evaporate. If the polymeric surface layer 110 seen in FIG. 4 is provided as a coating, the preferred material should be easily solvated and compatible with the underlying balloon material. The preferred material for the coated surface layer 110 seen in FIG. 4 is a high friction elastomeric polymer such as poly(vinyl acetate) with a mole weight of 140,000 at 100 mg/ml in acetone (available from Aldrich Chemicals in Milwaukee, Wis.). Other suitable materials for delivering the surface layer 110 as a coating include silicone based polymers such as NuSil 1081 (available from NuSil Technology located in Carpinteria, Calif.) at 10% in 1:1 ethyl acetate:acetone. Coatings such as poly(vinyl acetate) are preferable to silicone based pressure sensitive adhesives because silicone based pressure sensitive adhesives may attract and hold more foreign matter, e.g., dust and lint, than is desirable.

Another method of providing a high friction surface is to coaxially extrude an elastomeric polymer as an outer layer of the material being extruded as balloon tubing. If the polymeric surface layer 110 is provided as a coaxial extrusion, the preferred material will be compatible with the underlying balloon material as well as exhibit a comparable melt index. The preferred material for a coaxially extruded polymeric surface layer 110 seen in FIG. 4 is a high friction elastomeric polymer such as poly(ethylene vinyl acetate) with a melt index of 3.0 (available as Elvax 265 from E.I. Du Pont de Nemours & Company, Wilmington, Del.).

Regardless of the method of providing the polymeric surface layer 110, materials with lower melt temperatures than LDPE, such as poly(vinyl acetate) and poly(ethylene vinyl acetate), are preferable because they allow the stent to become embedded at lower temperatures with less balloon shrinkage and less potential for damage to the balloon. Polymers exhibiting greater elasticity than LDPE, such as poly(vinyl acetate) and poly(ethylene vinyl acetate), are preferred since they place less restraint on compliant balloons and are less likely to fracture or delaminate during balloon expansion. The resulting balloon should have an outer surface that has a coefficient of friction high enough to prevent the stent from sliding along the balloon prior to and during the PTCA procedure, but not have so high a coefficient of friction as to inhibit proper release and deployment of the stent.

The thickness of the polymeric surface layer 110 may range from a few monolayers for a coating up to 0.002 inches depending on the material and the method of delivery. The overall inner diameter of a typical balloon tube is approximately 0.020 inches. The overall outer diameter of the balloon 35 is 0.0405 inches. If a coaxial extrusion of the surface layer 110 is employed, the wall thickness of the outer layer 110 is approximately 0.002 inches while the thickness of the underlying LDPE layer 120 is approximately 0.00825 inches. The surface layer 110 should constitute about 20% of the balloon tube thickness for coaxial extrusions.

The preceding specific embodiments are illustrative of the practice of the invention. It is to be understood, however, that other expedients known to those skilled in the art or disclosed herein, may be employed without departing the scope of the appended claims.

| No. | Component |
| --- | --- |
| 20 | Stent |
| 25 | Peak |
| 30 | Valley |
| 35 | Balloon |
| 40a–f | Element |
| 45 | Marker Band |
| 50 | End Loop |
| 55 | Ridges |
| 60 | Guidewire Lumen |
| 65 | Inflation Lumen |
| 70 | Shaft |
| 75 | Heat Chamber |
| 80 | Guidewire Tube |
| 85 | Crimper with embedded wire |
| 90 | Embedded Wire |
| 95 | Probe |
| 100 | Crimper with Embedded Probe |
| 105 | Embedded Probe |
| 110 | Polymeric Surface Layer |
| 120 | Underlying Layer |

What is claimed is:

1. A method of making an intravascular catheter system for implanting a radially expandable stent within a body vessel comprising:

providing a catheter having a shaft defining an inflation lumen having a proximal end and a distal end, an inflatable balloon having a proximal end and a distal end, the balloon proximal end being sealingly affixed to the distal end of the shaft, the balloon being a fluid communication with the inflation lumen, the balloon having an outer diameter and a wall thickness, the balloon having a surface layer over an underlying layer, the surface layer having a lower melt temperature than the underlying layer such that heating the surface layer will not damage the underlying layer;

providing a stent, the stent having a thickness and being formed of a helically wound wire having longitudinally movable elements, the wire being wound into a zig-zag pattern; and mounting the stent coaxially upon the outer diameter of the balloon, a portion of the stent thickness being recessed into the balloon by heating the stent to form areas sized to receive the helically wound wire and defined by a permanent first and second ridge deformation in the outer diameter of the balloon in the outline of the stent for receiving the portion of the stent thickness so as to reduce stent slippage or snagging and to cause the balloon to expand evenly and the stent to deploy uniformly.

2. A method of manufacture according to claim 1 wherein a temperature of 76 degrees C. is applied to the stent for one-and-one-half minutes.

3. A method of manufacture according to claim 1 wherein the ridges formed are less than 50 percent of the balloon wall thickness.

4. A method of manufacture according to claim 1 wherein the ridges are impressed into the surface layer, the surface layer having a sufficient coefficient of friction against the stent so as to reduce stent slippage and cause the balloon to expand evenly and the stent to deploy uniformly.

5. A method of manufacture according to claim 1 wherein the stent material is tantalum.

6. A method of manufacture according to claim 1 wherein the surface layer is provided of a material consisting of an elastomeric polymer.

7. A method of manufacture according to claim 4 including a step wherein the surface layer is coated upon the balloon.

8. A method of manufacture according to claim 4 including a step wherein the surface layer is coaxially extruded.

* * * * *